United States Patent
Veyrat

(10) Patent No.: US 7,754,115 B2
(45) Date of Patent: Jul. 13, 2010

(54) CERAMIC DENTAL PROSTHESIS, METHOD AND DEVICE FOR MAKING SAME

(76) Inventor: Germinal Veyrat, 104 cours Albert Thomas, Lyon (FR) 69008

( * ) Notice: Subject to any disclaimer, the term of this patent is extended or adjusted under 35 U.S.C. 154(b) by 90 days.

(21) Appl. No.: 11/909,864

(22) PCT Filed: Mar. 31, 2006

(86) PCT No.: PCT/FR2006/000706

§ 371 (c)(1),
(2), (4) Date: Sep. 27, 2007

(87) PCT Pub. No.: WO2006/103357

PCT Pub. Date: Oct. 5, 2006

(65) Prior Publication Data

US 2008/0193900 A1    Aug. 14, 2008

(30) Foreign Application Priority Data

Mar. 31, 2005   (FR) .................................. 05 03387

(51) Int. Cl.
| A61C 13/08 | (2006.01) |
| A61C 13/00 | (2006.01) |
| A61C 13/20 | (2006.01) |
| A61C 13/10 | (2006.01) |
| B28B 1/00 | (2006.01) |
| B28B 3/00 | (2006.01) |
| B28B 5/00 | (2006.01) |
| C04B 33/32 | (2006.01) |
| C04B 33/36 | (2006.01) |
| C04B 35/64 | (2006.01) |

(52) U.S. Cl. .............................. 264/19; 264/16; 264/17; 264/18; 264/603; 264/650

(58) Field of Classification Search ............. 264/16–20, 264/603, 650; 425/2
See application file for complete search history.

(56) References Cited

U.S. PATENT DOCUMENTS

| 4,431,451 | A | * | 2/1984 | Mabie et al. .................. 106/35 |
| 4,562,882 | A | * | 1/1986 | Alleluia ...................... 164/529 |
| 4,592,890 | A | * | 6/1986 | Burnett et al. .............. 420/442 |
| 5,346,396 | A | * | 9/1994 | Hakamatsuka .............. 433/208 |
| 5,447,967 | A | * | 9/1995 | Tyszblat ..................... 523/116 |
| 5,968,424 | A | * | 10/1999 | Shimosawa et al. ........... 264/19 |
| 6,059,949 | A | * | 5/2000 | Gal-Or et al. ............... 204/484 |
| 6,488,503 | B1 | * | 12/2002 | Lichkus et al. ........... 433/202.1 |
| 6,626,672 | B1 | * | 9/2003 | Been .......................... 433/223 |
| 2002/0013636 | A1 | * | 1/2002 | O'Brien et al. ............. 700/118 |
| 2002/0017021 | A1 | * | 2/2002 | Panzera ..................... 29/896.1 |
| 2002/0175430 | A1 | * | 11/2002 | Glidewell .................... 264/16 |
| 2004/0026806 | A1 | * | 2/2004 | Wolz .......................... 264/16 |
| 2005/0204514 | A1 | * | 9/2005 | Takamatsu et al. ........ 23/305 R |

* cited by examiner

Primary Examiner—Khanh Nguyen
Assistant Examiner—Matthew Hoover
(74) Attorney, Agent, or Firm—William H. Eilberg

(57) ABSTRACT

A ceramo-ceramic dental prosthesis is made from a patient's negative mandibular impression, including at least one working cavity having an inner surface matching the lower surface of the prosthesis to be produced and left at least by one tooth primed by the dental surgeon to be prosthetized. The method of making the prosthesis includes a step of providing a single-unit wax model used for producing by precision casting a single-unit metal model on which is mounted, by the dental technician, a ceramic, the single-unit model having previously been coated with a stripping product to avoid the adherence of the ceramic on the metal single-unit model after the ceramic is cured on the single-unit metal model.

17 Claims, 5 Drawing Sheets

CERAMIC DENTAL PROSTHESIS, METHOD AND DEVICE FOR MAKING SAME

TECHNICAL FIELD OF THE INVENTION

The present invention concerns ceramic dental prostheses intended to be placed in the mouth of a patient.

There are known already such dental prostheses consisting of a metal coping covered with ceramic cemented to the dentine stump of the patient, conforming to the cervical boundary cut effected by the dental surgeon.

However, this kind of prosthesis has an imperfect esthetic because of the presence of the opaque metal and often because of shrinkage of the gum caused by the non-biocompatibility of the metal in the organism.

Furthermore, because of the high thermal conductivity of the metal part, the patient can suffer from intense thermal irritation of the gum.

A new type of dental prosthesis has therefore been developed, known as a ceramo-ceramic prosthesis, having no metal part and in which the coping is of ceramic. The absence of any metal part avoids the major drawbacks encountered with the previous solution.

During the production of a ceramo-ceramic prosthesis, the dental surgeon prepares the tooth for which a prosthesis must be produced by cutting it in an appropriate manner to receive an inlay-onlay, crown or veneer. Once this cutting has been completed, the dental surgeon takes an impression of the patient's dentition and sends it to the dental prosthetist to produce the dental prosthesis.

The dental prosthetist then produces a ceramic dental prosthesis intended to be fitted over or into the cut effected by the dental surgeon.

Such methods are known and very widely used by companies such as the companies VITA and IVOCLAR VIVADENT.

However, the conventional methods used at present for the production of ceramo-ceramic dental prostheses still have numerous drawbacks.

First of all, the current methods require major investment in highly advanced and dedicated equipment.

Moreover, these methods require the dental surgeon to cut the tooth very accurately, conforming to minimum thicknesses and specific angles of orientation of the cut surfaces. This is a very severe constraint. Cutting the tooth intended to receive a dental prosthesis is therefore very complicated. As the patient does not keep still throughout the intervention of the dental surgeon, the latter finds it difficult to assess the quality of the work of cutting the tooth that he is carrying out.

Another drawback is the complexity of the current methods. They require a very large number of steps with numerous and difficult parameters, which tends to multiply the possible sources of errors that can lead to the production of a dental prosthesis that is unsuitable for the patient. This results in frequent rejects, which means it takes longer to produce the prostheses and increases their average cost.

Apart from their very large number, the steps of the known methods are generally very long. In fact, manuals on these methods available to the public indicate a total time of 4 hours to 6 hours 30 minutes for the production of a dental prosthesis. This kind of duration singularly complicates the task of the dental prosthetist, who has to pass an entire day working on one and only one dental prosthesis.

The dental prosthetist is all the more constrained in that the smallest error in one of the numerous process steps can lead to him starting over again from the beginning. This results in a very considerable waste of time for the dental prosthetist, accompanied by a high level of stress that hardly contributes to the success of the dental prosthesis.

Finally, if a patient damages his dental prosthesis after it has been implanted in the mouth, to produce a new ceramic dental prosthesis the dental prosthetist must begin his work all over again without it being possible to save any time because of the work previously done during the production of the first dental prosthesis.

There is furthermore known from the document U.S. Pat. No. 6,488,503 B1 a method of producing ceramic dental prostheses in which a three-layer tooth is produced by three successive injections of ceramic: a first injection into a first mold cavity produces a core; the core is then molded over by a second injection into a second mold cavity; the whole is finally molded over by a third injection in a third mold cavity. The colors of the three ceramics injected are different. Such a method mass produces teeth having the same shape and the same appearance, which does not correspond to the reality of the requirement for restoration by means of dental prostheses. The teeth obtained have a regular appearance, with no differing surface areas, which does not correspond to the appearance of natural teeth either. Also, the method necessitates major investment in multiple molds.

SUMMARY OF THE INVENTION

A first problem addressed by the invention is that of considerably simplifying the method of producing a ceramo-ceramic dental prosthesis of satisfactory natural appearance, without requiring too constraining cutting of the tooth by the dental surgeon, and without requiring major investment by the dental prosthetist in very costly and dedicated equipment.

In another aspect, the invention aims to reduce significantly the time for the dental prosthetist to produce a dental prosthesis.

The invention also aims to improve the dimensional accuracy of the prostheses produced, in particular in the areas of the points of contact and in the peripheral prosthesis area corresponding to the boundary of the preparation of the tooth to be treated.

The invention further aims to enable even faster and accurate production of a second dental prosthesis for a patient if a first prosthesis should break in the mouth of that patient.

To achieve the above and other objects, the invention proposes a method of fabricating a ceramic dental prosthesis, produced from a negative mandibular impression of a patient including at least one working cavity having an interior surface conforming to the intrados of the prosthesis to be produced and formed by at least one tooth prepared by the dental surgeon to receive a prosthesis, the method comprising the following successive steps:

a) producing a single-unit wax model by casting a wax in said working cavity of the negative mandibular impression and forming a wax root part thereof projecting above the working cavity;

b) fixing a sprue that can be burned out to the summit of the root part of the single-unit wax model;

c) coating the single-unit wax model and the sprue that can be burned out in a coating device, for example in a cylinder as usually employed by dental prosthetists;

d) producing a single-unit metal model identical to the single-unit wax model by casting in the coating a metal alloy in place of the single-unit wax model and the sprue that can be burned out, the single-unit metal model therefore including a root sprue, a projecting root part and an extrados surface corresponding in positive form to the intrados of the tooth to be produced;

e) applying a stripping product to the extrados surface of the single-unit metal model to prevent adhesion of the ceramic to the metal after firing the ceramic on the single-unit metal model;

f) applying ceramic, for example a ceramic of the usual type for dental prostheses, to the single-unit metal model covered with the stripping product, so that the ceramic has an exterior shape identical to the tooth once the prosthesis has been fitted;

g) firing the ceramic carried by the single-unit metal model, for example as indicated by the ceramic supplier;

h) finishing the ceramic in terms of shape and tint and removing the single-unit metal model.

The single-unit metal model produced in this way has an extrados surface corresponding in positive form to the intrados of the tooth to be produced. This means that the upper part of the single-unit metal model is the exact replica of the tooth as prepared by the dental surgeon in the mouth of the patient.

The single-unit metal model is produced by a conventional lost-wax process, enabling parts to be produced with very accurate dimensions.

This method according to the invention, using a single-unit wax model and a single-unit metal model, also has the advantage of being much faster and much more reliable than the known methods referred to hereinabove. Thus it has been possible to produce ceramic prostheses according to the invention in less than two hours, generally in an hour and a quarter or an hour and a half, without rejects.

The ceramic can advantageously be built up in the usual manner by using a brush to apply a ceramic paste to the single-unit metal model after it has been covered with the stripping product. Thus the dental prosthetist can very easily impart the required shape to the dental prosthesis. Furthermore, this enables the dental prosthetist to choose and apply different ceramic tints, where appropriate in separate surface areas, in order to approximate as closely as possible what will appear natural in the mouth of the patient. Also, the dental prosthetist can adapt the tint of each of the layers of ceramic paste constituting the prosthesis, which gives him greater possibilities of reproducing the esthetic appearance of a natural tooth.

The stripping product applied to the extrados surface of the single-unit metal model enables the ceramic produced by the dental prosthetist to be detached from the single-unit metal model after firing the ceramic on the single-unit metal model in the kiln. It is important that the ceramic and the single-unit metal model be separated as gently as possible in order not to damage the fired ceramic.

According to the invention, the metal alloy can be a dental alloy with a melting point higher than the firing temperature of the ceramic and with a coefficient of thermal expansion close to that of the ceramic.

The metal alloy having a melting point higher than the ceramic firing temperature, the single-unit metal model is not affected by firing the ceramic thereon in the kiln. Furthermore, the fact that the metal alloy has a coefficient of thermal expansion close to that of the ceramic makes it possible to produce a ceramic dental prosthesis free of breaks or cracks and the dimensions whereof correspond exactly to those of the tooth as prepared by the dental surgeon in the mouth of the patient. In fact, if the coefficients of thermal expansion of the metal alloy and the ceramic were very different, the ceramic could break or crack, or the single-unit metal model and the ceramic produced by the dental prosthetist could not be nested exactly with a good fit without force, which would mean that the ceramic would not fit exactly to the tooth as prepared by the dental surgeon in the mouth of the patient either.

According to the invention, the metal alloy can include nickel and chromium.

The addition of nickel to the metal alloy for the production of the single-unit metal model prevents excessive oxidation of the single-unit metal model, which oxidation could compromise subsequent use of the single-unit metal model.

During extraction of the single-unit metal model after step d), the model is advantageously carefully cleaned, for example by sandblasting, to remove all traces of coating.

Thorough cleaning of the exterior surface of the single-unit metal model is useful for the latter to correspond exactly to the tooth as prepared by the dental surgeon in the mouth of the patient. The presence of coating left on the exterior surface of the single-unit metal model could prevent the production of a ceramic dental prosthesis fitting exactly over the tooth as prepared by the dental surgeon in the mouth of the patient.

According to one embodiment of the invention, the stripping product for preventing adhesion of the ceramic to the metal during firing of the ceramic on the single-unit metal model is a mixture based on quartz powder.

The quartz powder can advantageously have a particle size of about 40 to 50 microns.

According to another preferred embodiment of the invention, the stripping product, for preventing adhesion of the ceramic to the metal during firing of the ceramic on the single-unit metal model, is the product ToothPCS marketed by the French company JBC LOGIDIS.

The stripping product applied to the extrados surface of the single-unit metal model enables the ceramic to be separated from the single-unit metal model, after the ceramic has been fired on the single-unit metal model in the kiln, with no force or stress liable to damage the fired ceramic.

The method advantageously further includes, between the steps e) and f), a dehydration step during which the single-unit metal model coated with the stripping product is placed in a ceramic kiln at about 400° C. for about one minute.

This dehydration step confers a powdery character on the stripping product applied to the extrados surface of the single-unit metal model. Thus the powdery product of very low adhesion to the extrados surface of the single-unit metal model will prevent the ceramic from continuing to adhere to the single-unit metal model after the ceramic is fired on the single-unit metal model.

The application of the stripping product to the single-unit metal model is advantageously effected so that it impinges slightly on the cervical boundary of the extrados surface of the single-unit metal model. Thus, during the step f) of building up the ceramic, for example using a brush, the dental prosthetist produces a mass of ceramic covering the whole of the extrados surface of the single-unit metal model and extending slightly below the cervical boundary, thus obtaining the correct dimension after shrinkage of the ceramic caused by firing it on the single-unit metal model.

According to another aspect of the invention, it may be envisaged that the method further includes, between steps d) and e), the production of a working model including the following steps:

d1) inserting the single-unit metal model in the working cavity of the mandibular impression;

d2) producing a working model by casting plaster in and on the mandibular impression in which the single-unit metal model is held;

d3) extracting the working model and removing from it the single-unit metal model.

This produces a working model in plaster into which the root part of the single-unit metal model with its root sprue is inserted. The single-unit metal model is then easy to extract from the working model, leaving the working model with a cavity into which the single-unit metal model can be reinserted very easily and very accurately.

The working model produced in this way and fitted with the single-unit metal model is a faithful replica of the dentition of the patient. The dental prosthetist can therefore use the working model to build up the ceramic in an esthetic manner that is harmonious with the patient's other teeth. Moreover, this enables the dental prosthetist to adjust the points of contact of the prosthesis with the adjoining teeth when building up the ceramic using a brush.

The withdrawal and/or insertion of the single-unit metal model from/in the working model are facilitated by the low oxidation thereof (as a result of the presence of nickel and chromium in the metal alloy used) and the great precision with which the latter is produced by the lost-wax molding process. In fact, oxidation of the single-unit metal model could lead to a variation of its exterior dimensions and/or of its surface state, complicating its insertion in and/or its withdrawal from the working model.

The working model and the single-unit metal model are stored in the dental prosthetist's laboratory, and he can therefore, using these items, easily and very quickly fabricate a new dental prosthesis for the patient should the latter accidentally break the first dental prosthesis produced. The dental prosthetist therefore obtains the benefit of the work that was previously carried out at the time of producing the first dental prosthesis for a patient, saving considerable time in the production of a second dental prosthesis identical to the first.

During the production of the working model with the single-unit metal model inserted into the working cavity of the mandibular impression, wax can advantageously be applied around the base of the projecting root part of the single-unit metal model, impinging slightly on the mandibular impression at the periphery of the working cavity.

Applying wax around the base of the projecting root part of the single-unit metal model when inserted into the mandibular impression holds it in place while molding the plaster impression. Furthermore, wax applied in this way prevents penetration of plaster into the working cavity in which the single-unit metal model is inserted.

According to the invention, a final presentation model can also be produced by casting plaster in and on the mandibular impression.

The final presentation model enables final verification of the appropriateness of the ceramic dental prosthesis so produced to the dentition of the patient as prepared by the dental surgeon. The esthetic effect can be verified, for example, and also the points of contact of the prosthesis with the adjoining teeth.

According to one aspect of the invention, the step g) of firing the ceramic is effected twice, with an intermediary step of rectification of shrinkage of the periphery of the ceramic in contact with the single-unit metal model.

The dental prosthesis is fired on the single-unit metal model in a standard ceramic kiln, which has the advantage that this does not oblige the dental prosthetist to invest in a costly dedicated kiln.

The intermediary step of rectification of shrinkage of the periphery of the ceramic in contact with the single-unit metal model is advantageously effected by adding neck mass in the region of the shrinkage.

The periphery of the ceramic is therefore perfectly contiguous with the cervical boundary of the extrados surface of the single-unit metal model, which thereafter ensures perfect nesting of the ceramic dental prosthesis over the tooth as prepared by the dental surgeon in the mouth of the patient.

According to the invention, the shape of the ceramic can be finished in step h) by grinding, where appropriate including checking it against the presentation model.

Grinding imparts its final shape to the prosthesis and it is possible to check that this shape is both esthetic and functional using the final presentation model. For example, it is important that the ceramic prosthesis once fitted does not injure the gum of the patient.

Thus the production of a dental prosthesis according to the invention does not necessitate any very costly and dedicated equipment not ordinarily already in the possession of a dental prosthetist. The raw materials used can also be of a standard type and not differ in any way from the materials usually employed by a dental prosthetist, apart from the stripping product.

According to the invention, the method of fabricating a ceramic dental prosthesis described here can be used for the production of an inlay-onlay, crown, veneer or bridge type dental prosthesis.

A ceramic dental prosthesis obtained by a method according to the invention can be recognizable in particular by the fact that, within the mass of ceramic, there are distinguished surface areas having stacks of successive thin layers, generally more than three layers, each layer resulting from application of material using a brush, and distinct surface areas that can have different layer colors and thicknesses.

The successive layers can be distinguished by different tints, but generally with no sharp interface following firing of the ceramic.

BRIEF DESCRIPTION OF THE DRAWINGS

Other objects, features and advantages of the present invention will emerge from the following description of particular embodiments, given with reference to the appended figures, in which.

DESCRIPTION OF THE PREFERRED EMBODIMENTS

Figure 1:
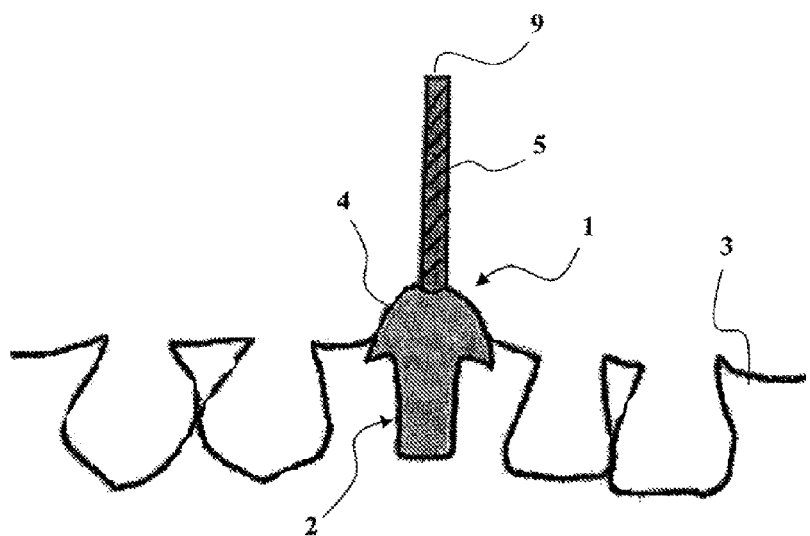
FIG. 1 is a diagrammatic view in section of a negative mandibular impression of a patient in which a single-unit wax model is produced.

FIG. 1 represents the production of a single-unit wax model 1 from a negative mandibular impression 3 that has been executed beforehand by a dental surgeon after preparation of the tooth to receive a prosthesis. The impression 3 comprises a working cavity 2 reproducing in negative form the shape of the prepared tooth. To produce the single-unit wax model, a dental wax is cast in the working cavity 2 of the negative mandibular impression 3. There is also formed in wax a root part 4 projecting above the working cavity 2. The dental wax used to produce the single-unit wax model 1 must not be a wax that is too hard and of high shrinkage, in order for it to espouse as closely as possible the shape of the working cavity 2.

The root part 4 projects above the working cavity 2 with a substantially conical shape. A sprue 5 that can be burned out is fixed to the summit of the root part 4 of the single-unit wax model 1. The sprue 5 that can be burned out is fixed simply by pressing it 1 to 2 mm into the root part 4.

Figure 2:
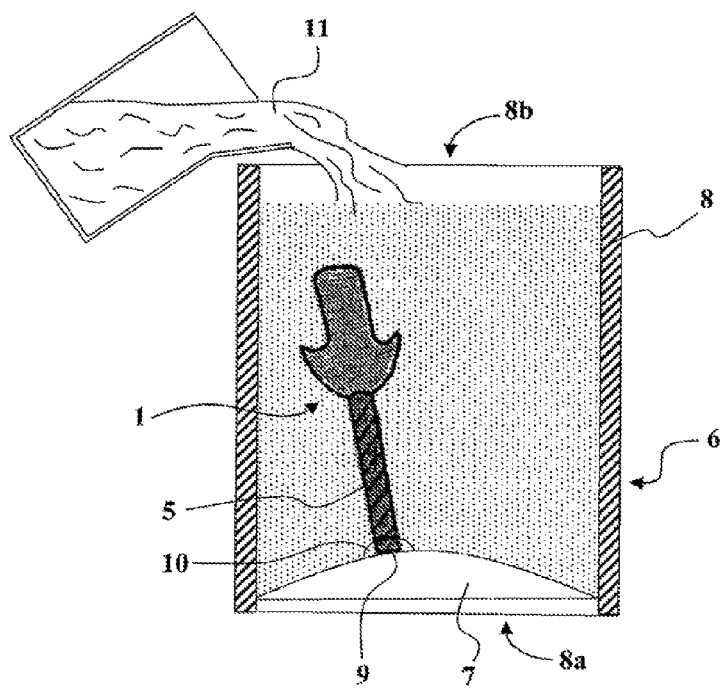
FIG. 2 is a diagrammatic view in section of the process of coating the single-unit wax model from FIG. 1.

FIG. 2 represents the coating of the single-unit wax model 1 in a conventional coating device 6. The coating device 6 includes a base 7 that obstructs in sealed manner the lower face 8a of a mold 8 generally called a cylinder. The free end 9 of the sprue 5 that can be burned out of the single-unit wax model 1 is stuck to the base 7 by means of a droplet of wax 10. The single-unit wax model 1 and the sprue 5 that can be burned out are then coated by casting a coating 11 in the cylinder 8 via the open top face 8b of the coating device 6. The coating 11 can be a standard coating used by dental prosthetists.

During coating, it is standard practice to pressurize the coating 11 so that, once solidified, the coating 11 is bubble-free and has a good surface state all around the single-unit wax model 1.

Once the coating 11 has solidified in the cylinder 8 all around the single-unit wax model 1 and the sprue 5 that can be burned out, the coating device 6 is placed in an kiln at a temperature chosen according to the instructions of the coating fabricator, in order to burn out the sprue 5 that can be burned out and evacuate the wax. The coating device 6 is then turned over and put down on the top face 8b of the cylinder 8. The base 7 is then directed upward and serves as a cone for casting the metal alloy.

On casting metal alloy in the base 7, the molten metal alloy takes the place of the sprue 5 that can be burned out and the wax in the solidified coating 11, taking on the exact shape of the single-unit wax model 1. This is the lost-wax process well known to dental prosthetists.

Figure 3:
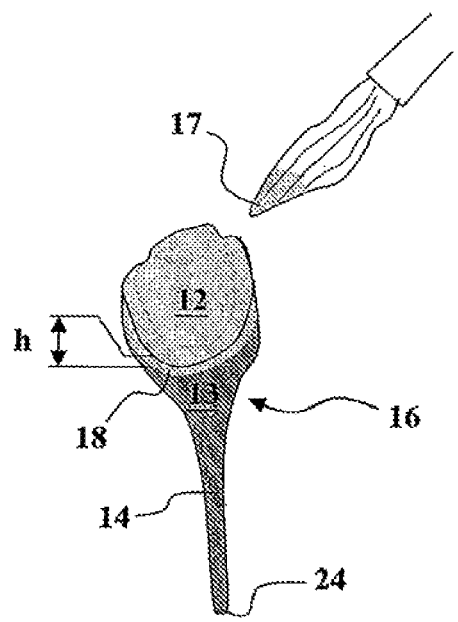
FIG. 3 is a perspective view of the single-unit metal model.

FIG. 3 represents the single-unit metal model 16 obtained by this method. It has an extrados surface 12, a root surface 13 and a root sprue 14. The extrados surface 12 of the single-unit metal model 16 corresponds in positive form to the intrados of the tooth prosthesis to be produced.

FIG. 3 also shows application of a stripping product 17 for preventing the ceramic adhering to the single-unit metal model 16 after firing the ceramic on the single-unit metal model 16 to the extrados surface 12 of the single-unit metal model 16 by means of a brush. The stripping product 17 is applied to the single-unit metal model 16 so that it extends a short distance beyond the extrados surface 12 of the single-unit metal model 16. An upper periphery 18 of low height h of the root surface 13 is therefore very lightly coated with stripping product 17. Then, this enables the dental prosthetist to use a brush to build up the ceramic on the single-unit metal model 16 coated with the stripping product 17, extending a very short distance beyond the extrados surface 12 onto the root surface 13 in order to be certain that the extrados surface 12 is covered with ceramic.

Despite the ceramic extending onto a very small part of the root surface 13, no bonding area between the ceramic and the single-unit metal model 16 is created after firing the ceramic because the stripping product 17 was also applied so as to extend onto the root surface 13 in the upper periphery 18 of low height h.

The stripping product 17 can be a mixture based on quartz powder. The quartz powder can have a particle size from about 40 to 50 microns. However, the stripping product 17 can also advantageously be a mixture marketed under the trade name ToothPCS by the French company JBC LOGIDIS.

Figure 4:
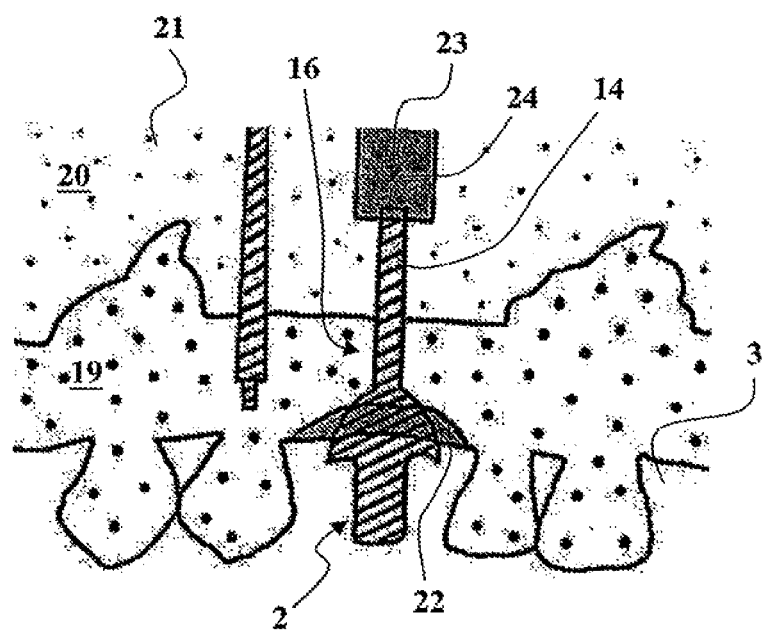
FIG. 4 is a diagrammatic view in section showing the production of a working model.

FIG. 4 represents the production of a working model 21. The extrados surface 12 of the single-unit metal model 16 is inserted in the working cavity 2 of the mandibular impression 3. A first layer 19 of class IV plaster and a second layer 20 of class III plaster are then cast, as is standard practice for dental prosthetists.

After drying, the working model 21 can be stripped from the mandibular impression 3. There is then obtained a working model 21 similar to that represented in FIG. 5, into which the single-unit metal model 16 can be inserted. It is then possible to separate the single-unit metal model 16 from the working model 21, which then incorporates a cavity 15 into which the dental prosthetist can conveniently re-insert the single-unit metal model 16. To facilitate such re-insertion, the metal alloy used to produce the single-unit metal model 16 can include nickel and chromium. The presence of nickel prevents excessive oxidation of the single-unit metal model 16 that could compromise its re-insertion in the working model 21.

When producing the working model 21 with the single-unit metal model 16 inserted in the mandibular impression 3 (FIG. 4), wax 22 is advantageously applied around the base of the root surface 13, extending a short distance onto the mandibular impression 3 at the periphery of the working cavity 2.

This wax 22 holds the single-unit metal model 16 in the mandibular impression 3 while casting the plaster, and prevents the class IV plaster 19 penetrating into the working cavity 2 under the single-unit metal model.

Furthermore, to make it easier for the dental prosthetist to locate the root sprue 14 of the single-unit metal model 16, a dab of wax 23 is applied to the free end 24 of the root sprue 14.

Once the working model 21 has been stripped from the impression, the dental prosthetist removes the wax 23 to uncover the end 24 of the root sprue 14. Removal of the single-unit metal model 16 from the working model 21 can be assisted by applying slight pressure to the end 24 of the root sprue 14 and slight traction to the extrados surface 12 of the single-unit metal model 16.

Figure 5:
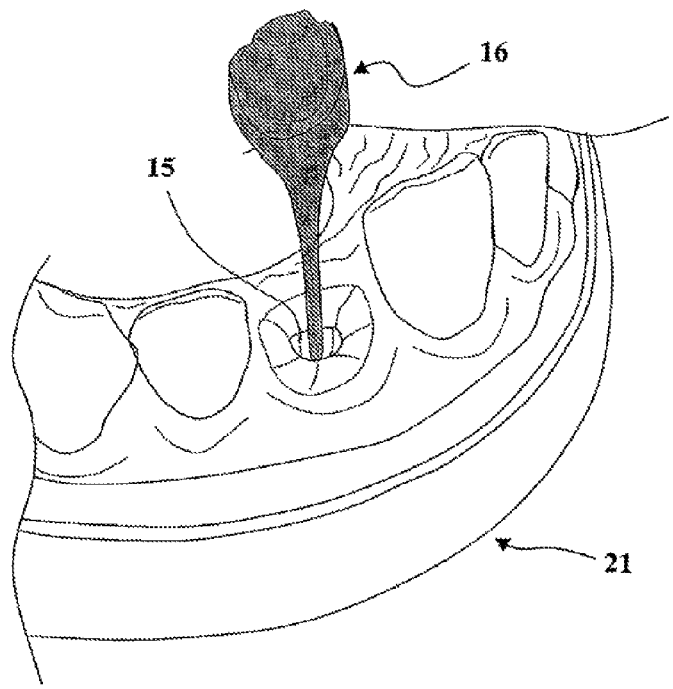
FIG. 5 is a perspective view of a working model according to the invention.

FIG. 5 shows a working model 21, once produced, into which the single-unit metal model 16 can be freely inserted or from which it can be freely withdrawn.

The working model 21 can thereafter be used by the dental prosthetist to hold the single-unit metal model 16 while he coats it with stripping product 17 and then while he builds up the ceramic on the single-unit metal model 16 to give it the exterior shape required for the prosthesis to be produced.

The dental prosthetist can then remove the single-unit metal model 16 on which he has built up the ceramic from the working model 21 and complete the building up of the ceramic so that it overflows very slightly onto the root surface 13 of the single-unit metal model 16 as previously mentioned.

Figure 6:
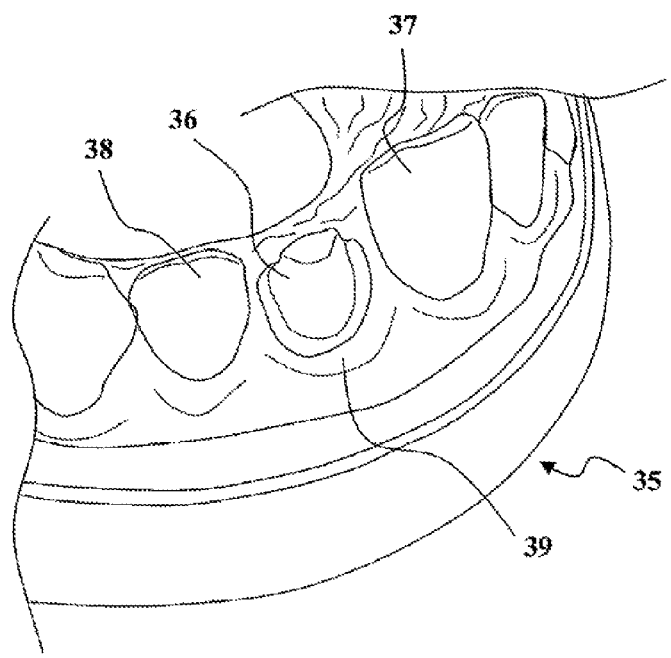
FIG. 6 is a perspective view of a final presentation module.

FIG. 6 represents a final presentation model 35 produced in the conventional way using the mandibular impression 3.

The final presentation model 35 is the exact replica in plaster of the dentition of the patient after preparation by the dental surgeon. It comprises in particular a cut tooth replica 36 and a replica of the adjacent teeth 37 and 38. The final presentation module 35 is used to check the points of contact of the ceramic prosthesis that caps the cut tooth replica 36. It is important to be able to check the points of contact of the ceramic prosthesis disposed on the cut tooth replica 36 with the replicas of the adjacent teeth 37 and 38. Furthermore, to ensure that the gum of the patient will not be injured by any projection from the ceramic prosthesis, the contact between the ceramic prosthesis and the gum replica 39 of the final presentation module 35 is checked. This ensures a perfect fit of the ceramic prosthesis onto the cut tooth replica 36.

Finally, the final presentation model 35 can serve as a support for the ceramic dental prosthesis when sending it to the dental surgeon.

Figure 7:
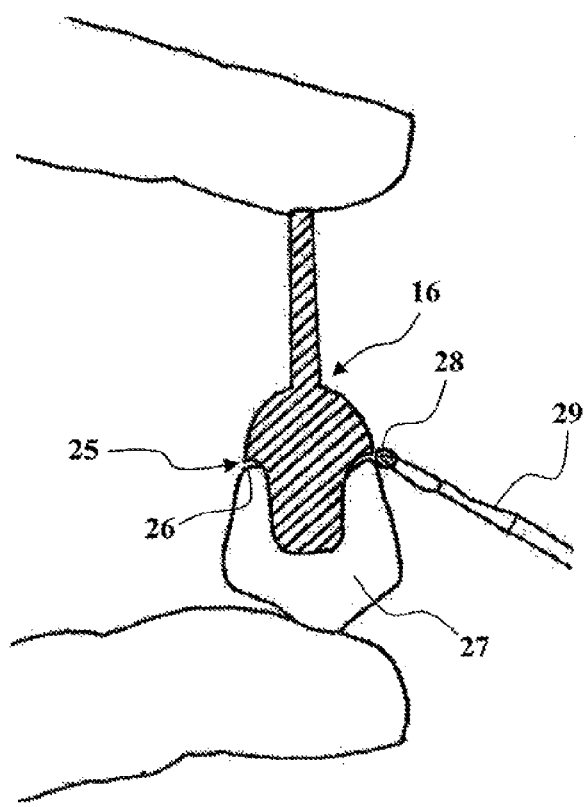
FIG. 7 is a view in section of a single-unit metal model to which a ceramic dental prosthesis in course of production is fitted.

FIG. 7 illustrates rectification of shrinkage 25 at the periphery 26 of the ceramic prosthesis 27 in contact with the single-unit metal model 16. This is an intermediary step between two successive steps of firing the ceramic prosthesis 27. This rectification of the shrinkage 25 is effected by using a brush 29 to add neck mass 28 at the level of the shrinkage 25.

Figure 8:
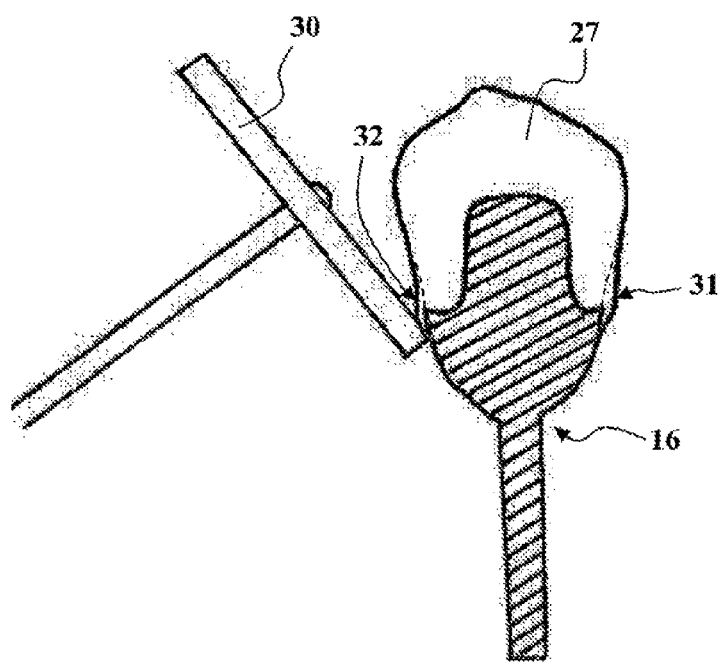
FIG. 8 is a diagrammatic view in section of the process of finishing a ceramic dental prosthesis on a single-unit metal model.

FIG. 8 illustrates finishing the shape of the ceramic prosthesis 27 by grinding using a rubber grinder wheel 30. The masses 31 and 32 are removed from the ceramic prosthesis 27 in order to be able, on the one hand, to separate the ceramic prosthesis 27 easily from the single-unit metal model 16 and, on the other hand, to impart to the ceramic prosthesis 27 the shape necessary for perfect nesting over the tooth in the mouth of the patient as prepared by the dental surgeon.

Figure 9:
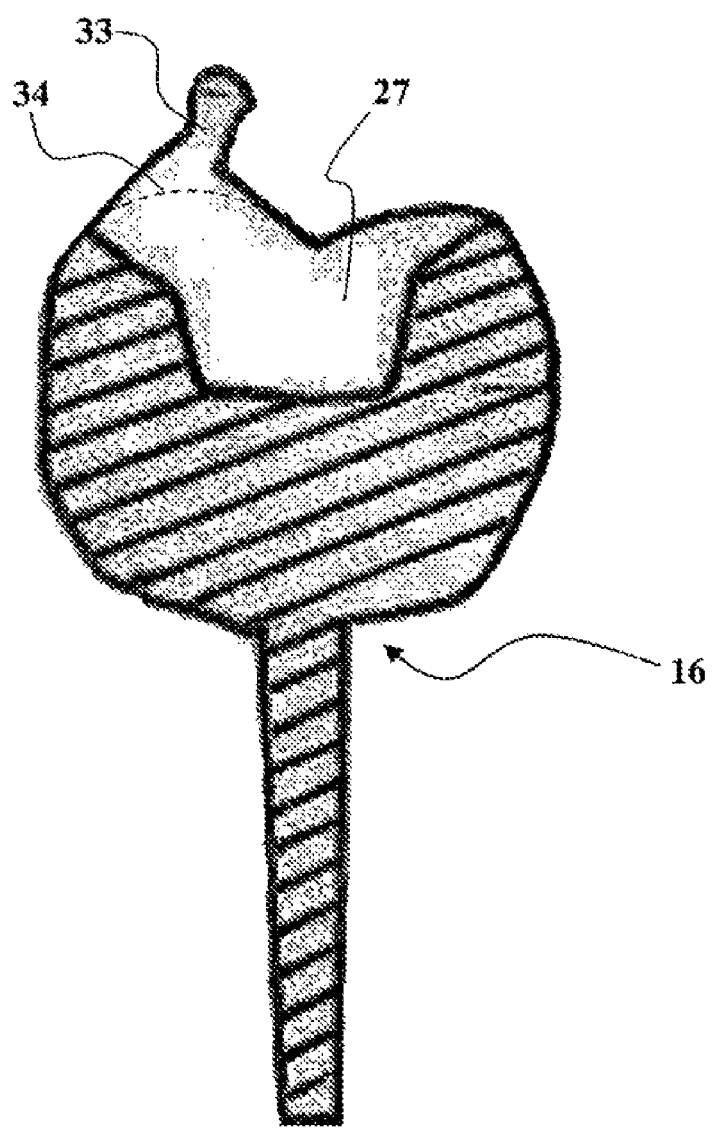
FIG. 9 is a diagrammatic view in section of an inlay-onlay type ceramic dental prosthesis fitted to a single-unit metal model.

FIG. 9 illustrates the production of a ceramic prosthesis 27 for a dental prosthesis in place on its single-unit metal model 16. The ceramic prosthesis 27 represented here is of a different type from that represented in the preceding figures: here it is an inlay-onlay type dental prosthesis.

In this figure, it is seen that during the step f) in which the dental prosthetist uses a brush to build up the ceramic 27 on the single-unit metal model 16, he adds an excrescence 33 to the top of the ceramic 27. This excrescence 33 enables the dental prosthetist to hold the ceramic 27 to separate the ceramic 27 from the single-unit metal model 16.

This excrescence 33 is ground off afterwards along the dashed line 34 in order to impart to the ceramic prosthesis 27 the final shape that it must have in the mouth of the patient.

The method according to the invention is therefore usable for all the various types of dental prosthesis that exist.

In all cases, the prosthesis obtained consists entirely of a mass of ceramic in which there can where appropriate be distinguished thin layers of different tint or appearance. In fact, to achieve the esthetic appearance of a natural tooth, the prosthetist may be required, when building up of the ceramic, to use the brush to superpose successive layers of different ceramics having different characteristics in terms of tint and translucency. The thickness of the layers corresponds to the usual thickness of a layer of ceramic deposited using a brush.

The present invention is not limited to the embodiments that have been described explicitly and encompasses diverse variants and generalizations thereof within the scope of the following claims.

The invention claimed is:

1. Method for fabricating a ceramo-ceramic dental prosthesis, produced from a negative mandibular impression of a patient including at least one working cavity having an interior surface conforming to the intrados of the prosthesis to be produced and formed by at least one tooth prepared by the dental surgeon to receive a prosthesis, comprising the following successive steps:
   a) producing a single-unit wax model by casting a wax in said working cavity of the negative mandibular impression and forming a wax root part thereof projecting above the working cavity;
   b) fixing a sprue that can be burned out to the summit of the root part of the single-unit wax model;
   c) coating the single-unit wax model and the sprue that can be burned out in a coating device;
   d) producing a single-unit metal model identical to the single-unit wax model by casting a metal alloy in the coating in place of the single-unit wax model and the sprue that can be burned out, the single-unit metal model therefore including a root sprue, a projecting root part and an extrados surface corresponding in positive form to the intrados of the tooth to be produced;
   e) applying a stripping product to the extrados surface of the single-unit metal model to prevent adhesion of the ceramic to the metal after firing the ceramic on the single-unit metal model;
   f) building up ceramic on the single-unit metal model covered with the stripping product, so that the ceramic has an exterior shape identical to the tooth once the prosthesis has been fitted;
   g) firing the ceramic carried by the single-unit metal model;
   h) finishing the ceramic in terms of shape and tint and removing the single-unit metal model.

2. Method according to claim 1, wherein the metal alloy is a dental alloy with a melting point higher than the firing temperature of the ceramic and with a coefficient of thermal expansion close to that of the ceramic.

3. Method according to claim 1, wherein the metal alloy includes nickel and chromium.

4. Method according to claim 1, wherein, during extraction of the single-unit metal model after the step d), the latter is carefully cleaned, to remove all traces of coating.

5. Method according to claim 1, wherein the stripping product for preventing adhesion of the ceramic to the metal during firing of the ceramic on the single-unit metal model is a mixture based on quartz powder.

6. Method according to claim 5, wherein the quartz powder has a particle size of about 40 to 50 microns.

7. Method according to claim 1, further including between steps e) and f) a dehydration step during which the single-unit metal model coated with the stripping product is placed in a ceramic kiln at about 400° C. for about one minute.

8. Method according to claim 1, wherein the stripping product is applied to the single-unit metal model so that it extends a short distance beyond the cervical boundary of the extrados surface of the single-unit metal model.

9. Method according to claim 1, further including between steps d) and e) the production of a working model by the following steps:
   d1) inserting the single-unit metal model in the working cavity of the mandibular impression;
   d2) producing a working model by casting plaster in and on the mandibular impression in which the single-unit metal model is held;
   d3) extracting the working model and removing the single-unit metal model from it.

10. Method according to claim 9, wherein, during the production of the working model with the single-unit metal model inserted into the working cavity of the mandibular impression, wax is applied around the base of the projecting root part of the single-unit metal model extending a short distance onto the mandibular impression at the periphery of the working cavity.

11. Method according to claim 1, further including the production of a final presentation model by casting plaster in and on the mandibular impression.

12. Method according to claim 1, wherein the step g) of firing the ceramic is effected twice, with an intermediary step of rectification of shrinkage of the periphery of the ceramic in contact with the single-unit metal model.

13. Method according to claim 12, wherein the intermediary step of rectification of shrinkage of the periphery of the ceramic in contact with the single-unit metal model is effected by adding neck mass in the region of the shrinkage.

14. Method according to claim 1, wherein the shape of the ceramic is finished in the step h) by grinding, possibly in combination with checking against the presentation model.

15. A method according to claim 1, further comprising using the method for the production of an inlay-onlay, crown, veneer or bridge type dental prosthesis.

16. Method for fabricating a ceramic dental prosthesis, produced from a negative mandibular impression of a patient including at least one working cavity having an interior surface conforming to the intrados of the prosthesis to be produced and formed by at least one tooth prepared by the dental surgeon to receive a prosthesis, comprising the following successive steps:
a) producing a single-unit wax model by casting a wax in said working cavity of the negative mandibular impression and forming a wax root part thereof projecting above the working cavity;
b) fixing a sprue that can be burned out to the summit of the root part of the single-unit wax model;
c) coating the single-unit wax model and the sprue that can be burned out in a coating device;
d) producing a single-unit metal model identical to the single-unit wax model by casting a metal alloy in the coating in place of the single-unit wax model and the sprue that can be burned out, the single-unit metal model therefore including a root sprue, a projecting root part and an extrados surface corresponding in positive form to the intrados of the tooth to be produced;
e) applying a stripping product to the extrados surface of the single-unit metal model to prevent adhesion of the ceramic to the metal after firing the ceramic on the single-unit metal model;
f) building up ceramic on the single-unit metal model covered with the stripping product, so that the ceramic has an exterior shape identical to the tooth once the prosthesis has been fitted;
g) firing the ceramic carried by the single-unit metal model;
h) finishing the ceramic in terms of shape and tint and removing the single-unit metal model,
wherein the stripping product for preventing adhesion of the ceramic to the metal during firing of the ceramic on the single-unit metal model is a mixture based on quartz powder.

17. Method according to claim 16, wherein the quartz powder has a particle size of about 40 to 50 microns.

\* \* \* \* \*